United States Patent
Brock et al.

(10) Patent No.: US 11,052,053 B2
(45) Date of Patent: Jul. 6, 2021

(54) NANOPARTICLE COMPRISING A BIO-RESORBABLE POLYESTER, A HYDROPHILIC POLYMER AND AN ACYLATED HUMAN LACTOFERRIN-DERIVED PEPTIDE

(71) Applicant: Evonik Operations GmbH, Essen (DE)

(72) Inventors: Roland Brock, Kalkar (DE); Rike Nabbefeld, Cologne (DE); Silko Grimm, Rossdorf (DE); Anne Benedikt, Frankfurt (DE); Andrea Engel, Birmingham, AL (US); Alexander Henrik Baron van Asbeck, Nijmegen (NL); Jürgen Dieker, Zutphen (NL)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/052,947

(22) PCT Filed: Apr. 24, 2019

(86) PCT No.: PCT/EP2019/060410
§ 371 (c)(1),
(2) Date: Nov. 4, 2020

(87) PCT Pub. No.: WO2019/214939
PCT Pub. Date: Nov. 14, 2019

(65) Prior Publication Data
US 2021/0137847 A1   May 13, 2021

(30) Foreign Application Priority Data
May 8, 2018   (EP) .................................... 18171195

(51) Int. Cl.
*A61K 9/51* (2006.01)
*A61K 9/50* (2006.01)
*A61K 9/14* (2006.01)
*A61K 49/00* (2006.01)

(52) U.S. Cl.
CPC ............ *A61K 9/5153* (2013.01); *A61K 9/146* (2013.01); *A61K 9/5031* (2013.01); *A61K 49/0041* (2013.01); *A61K 49/0056* (2013.01); *A61K 49/0093* (2013.01); *Y10S 977/773* (2013.01); *Y10S 977/906* (2013.01)

(58) Field of Classification Search
CPC .................................................. A61K 9/5153
See application file for complete search history.

(56) References Cited

U.S. PATENT DOCUMENTS

| 5,610,266 | A  | 3/1997  | Buchholz |
| 6,706,854 | B2 | 3/2004  | Buchholz et al. |
| 8,313,778 | B2 | 11/2012 | Seiler et al. |
| 9,156,942 | B2 | 10/2015 | Enderle et al. |
| 9,403,884 | B2 | 8/2016  | Brock et al. |
| 9,480,654 | B2 | 11/2016 | Seiler et al. |
| 9,724,422 | B2 | 8/2017  | Hartwig et al. |
| 2007/0014848 | A1 | 1/2007  | Buchholz et al. |
| 2009/0011038 | A1* | 1/2009 | Seiler ................... A61K 9/1641 424/501 |
| 2010/0061932 | A1 | 3/2010  | Brock et al. |
| 2010/0137550 | A1 | 6/2010  | Enderle et al. |
| 2011/0144301 | A1 | 6/2011  | Enderle et al. |
| 2011/0288267 | A2 | 11/2011 | Enderle et al. |
| 2013/0108662 | A1 | 5/2013  | Brock et al. |
| 2013/0273163 | A1 | 10/2013 | Seiler et al. |
| 2013/0302342 | A1 | 11/2013 | Hartwig et al. |
| 2014/0037722 | A1 | 2/2014  | Mousa et al. |
| 2016/0151504 | A1 | 6/2016  | Brock et al. |

FOREIGN PATENT DOCUMENTS

| CA | 2 472 648 | 12/2010 |
| EP | 0 427 185 | 10/1997 |
| EP | 1 468 035 | 7/2005 |
| EP | 1 907 023 | 11/2011 |
| EP | 2 263 707 | 2/2013 |
| EP | 2 147 036 | 3/2017 |
| WO | 2007/009919 | 1/2007 |
| WO | 2007/048599 | 5/2007 |
| WO | 2007/076904 | 7/2007 |
| WO | 2012/069089 | 5/2012 |
| WO | 2013/063695 | 5/2013 |
| WO | 2015/181138 | 12/2015 |
| WO | WO-2015181138 A1 * | 12/2015 ........... A61K 9/5153 |

OTHER PUBLICATIONS

Dagmar Zweytick et al. "Influence of N-acylation of a peptide derived from human lactoferricin on membrane selectivity." Biochimica et Biophysica Acta, vol. 1758 (2006) pp. 1426-1435. (Year: 2006).*

(Continued)

*Primary Examiner* — Isaac Shomer
(74) *Attorney, Agent, or Firm* — Grüneberg and Myers PLLC

(57) ABSTRACT

A nanoparticle includes a core. The core includes a bio-resorbable polyester and a hydrophilic polymer. The hydrophilic polymer is a portion of the bio-resorbable polyester or a separate polymer. An acylated human lactoferrin-derived peptide is coated onto the core. The acylated human lactoferrin-derived peptide is a peptide with the amino acid sequence SEQ ID NO. 1: KCFQWQRNMRKVRGPPVSCIKR or an amino acid sequence, which does not differ by more than 8 amino acid positions from the sequence SEQ ID NO: 1. The N-terminus of the human lactoferrin-derived peptide is acylated with a $C_{16}$-monoacyl group.

20 Claims, No Drawings

Specification includes a Sequence Listing.

(56) References Cited

OTHER PUBLICATIONS

Margherita Di Pisa, Gérard Chassaing, and Jean-Marie Swiecicki. "When cationic cell-penetrating peptides meet hydrocarbons to enhance in-cell cargo delivery." Journal of Peptide Science, vol. 21, 2015, pp. 356-369. (Year: 2015).*
Jianian Chen, Shaoshun Li, Qi Shen. "Folic acid and cell-penetrating peptide conjugated PLGA-PEG bifunctional nanoparticles for vincristine sulfate delivery." European Journal of Pharmaceutical Sciences 47 (2012), pp. 430-443. (Year: 2012).*
Erez Koren and Vladimir P. Torchilin. "Cell-penetrating peptides: breaking through to the other side." Trends in Molecular Medicine, Jul. 2012, vol. 18, No. 7, pp. 385-393. (Year: 2012).*
Malvern Instruments. https://www.materials-talks.com/wp-content/uploads/2014/07/FAQ-What-is-z-average.pdf accessed Apr. 20, 2021, 2 printed pages. (Year: 2021).*
U.S. Appl. No. 12/159,226, filed Dec. 1, 2008, Brock et al.
U.S. Appl. No. 14/955,696, filed Dec. 1, 2015, Brock et al.
International Search Report dated Aug. 6, 2019 in PCT/EP2019/060410.
Written Opinion dated Aug. 6, 2019 in PCT/EP2019/060410.
European Search Report dated Nov. 22, 2018 in European Application No. 18171195.3.
Hassert et al., "*On-Resin Synthesis of an Acylated and Fluorescence-Labeled Cyclic Integrin Ligand for Modification of Poly(lactic-co-glycolic acid)*," Chemistry & Biodiversity, 2012, 9(11), 2648-2658.
Wakayabashi et al., "*Inhibition of Iron/Ascorbate-Induced Lipid Peroxidation by an N-Terminal Peptide of Bovine Lactoferrin and Its Acylated Derivatives*," Biosci. Biotechnol, Biochem., 63 (5), 955-957,1999.

\* cited by examiner

NANOPARTICLE COMPRISING A BIO-RESORBABLE POLYESTER, A HYDROPHILIC POLYMER AND AN ACYLATED HUMAN LACTOFERRIN-DERIVED PEPTIDE

CROSS-REFERENCE TO RELATED APPLICATIONS

This application is a National Stage entry under § 371 of International Application No. PCT/EP2019/060410, filed on Apr. 24, 2019, which claims the benefit of European Application No, 18171195.3, filed on May 8, 2018. The content of each of these applications is hereby incorporated by reference in its entirely.

REFERENCE TO A SEQUENCE LISTING

The instant application contains a Sequence Listing which has been filed electronically in ASCII format and is hereby incorporated by reference in its entirety. Said ASCII copy, created on Oct. 14, 2020, is named "2020-10-14-Sequence-Listing.txt" and is 649 bytes in size.

BACKGROUND OF THE INVENTION

Field of the Invention

The present application is concerned with a nanoparticle comprising a bio-resorbable polyester, a hydrophilic polymer and an acylated human lactoferrin-derived peptide.

Description of Related Art

Lactic acid polymers, like for instance poly(D,L-lactide-co-glycolide)copolymers (PLGA), are biodegradable polymers and well known in the art for example from EP1468035, U.S. Pat. No. 6,706,854, WO2007/009919A2, EP1907023A, EP2263707A, EP2147036, EP0427185 or U.S. Pat. No. 5,610,266.

Human lactoferrin-derived peptides with an amino acid sequence according to SEQ. ID. No. 1 KCFQWQRNMRKVRGPPVSCIKR as disclosed herein are known from WO 2007/048599, WO 2007/076904A1, WO 2012/069089 and WO2015181138A1.

WO2015/181138A1 describes nanoparticles, based on calcium-phosphate nanoparticle core, an active ingredient, a lactic acid polymer coating and a cationic polymer coating including human lactoferrin-derived peptides.

Hassert et al. ((2012) Chemistry & Biodiversity Vol. 9 pp. 2648-2658) describes the "On-Resin Synthesis of an Acylated and Fluorescence-Labeled Cyclic Integrin Ligand for modification of Poly(lactic-co-glycolic acid)". Lipidated peptide was used to include a second functionality for coating of PLGA. A palmitoylated integrin-lipopeptide showed high affinity to PLGA.

BRIEF SUMMARY OF THE INVENTION

The invention is concerned with a nanoparticle comprising a core, comprising a bio-resorbable polyester and a hydrophilic polymer, wherein the hydrophilic polymer is a portion of the bio-resorbable polyester or a separate polymer, and, onto the core, an acylated human lactoferrin-derived peptide, wherein the acylated human lactoferrin-derived peptide is a peptide with the amino acid sequence SEQ ID No. 1: KCFQWQRNMRKVRGPPVSCIKR or an amino acid sequence, which does not differ by more than 8 amino acid positions from the sequence SEQ. ID. No. 1 and wherein the N-terminus of the human lactoferrin-derived peptide is substituted with a $C_{16}$-monoacyl group. Human lactoferrin-derived peptides (hLFF) may generally show a biological cell penetrating function (cell penetrating peptide (CPP), s. for instance WO 2007/048599 or WO 2007/076904A1) which means when delivered simultaneously with an active pharmaceutical ingredient (API) to human cells the human lactoferrin-derived peptides facilitates and promotes the uptake of the API in the cells.

The inventors have surprisingly found, that the combination of a $C_{16}$-acylated human lactoferrin-derived peptide with the amino acid sequence SEQ ID No. 1: KCFQWQRNMRKVRGPPVSCIKR or a sequence, which does not differ by more than 8 amino acid positions from the sequence SEQ. ID. No. 1, as a coating in a nanoparticle, based on a bio-resorbable polyester and a hydrophilic polymer is superior to corresponding nanoparticles comprising none-acylated or differently acylated human lactoferrin-derived peptides. Especially the relative fluorescence (per 100 A549 lung carcinoma cells) of Lumogen F305-fluorescent labelled nanoparticles is superior compared to other Lumogen F305-fluorescent labelled nanoparticles comprising coatings with differently acylated-hLFF-peptides or nanoparticles without a hLFF-coating.

DETAILED DESCRIPTION OF THE INVENTION

Nanoparticle

The invention is concerned with a nanoparticle comprising a core, comprising a bio-resorbable polyester and a hydrophilic polymer, wherein the hydrophilic polymer is a portion of the bio-resorbable polyester or a separate polymer, and a coating onto the core, wherein the coating comprises an acylated human lactoferrin-derived peptide, wherein the acylated human lactoferrin-derived peptide is a peptide with the amino acid sequence SEQ ID No. 1: KCFQWQRNMRKVRGPPVSCIKR or an amino acid sequence, which does not differ by more than 8 amino acid positions from the sequence SEQ. ID. No. 1 and wherein the N-terminus of the human lactoferrin-derived peptide is acylated with a $C_{16}$-monoacyl group.

Since the hydrophilic polymer may be present as a portion of the bio-resorbable polyester or as a separate polymer, there are four possible combinations of the bio-resorbable polyester and the hydrophilic polymer.

The nanoparticle comprising the bio-resorbable polyester and the hydrophilic polymer may be
i) a bio-resorbable polyester without a hydrophilic polymer portion and a hydrophilic polymer or
ii) a bio-resorbable polyester with a hydrophilic polymer portion or
iii) a bio-resorbable polyester with a hydrophilic polymer portion and a hydrophilic polymer or
iv) a bio-resorbable polyester without a hydrophilic polymer portion, a hydrophilic polymer and a bio-resorbable polyester with a hydrophilic polymer portion.

Ratio of the Bio-Resorbable Polyester to the Hydrophilic Polymer

The amount of the acylated human lactoferrin-derived peptide to the bio-resorbable polyester and the hydrophilic polymer is about 1 to 100% by weight or 5 to 75% by weight, preferably about 25 to 75% by weight.

Average Particle Size

The nanoparticles may have an average particle size (Z-Ave) in the range of about 50 to 900 nm, 50 to 300 nm, preferably from about 200 to 300 nm, most preferred from about 220 to 280 nm. The nanoparticles are usually of spherical shape.

Particle Size Distribution

The particle size distribution (PDI) of the nanoparticles may be in the range 0.5 or less, 0.05-0.3, 0.08-0.2, 0.09-0.19. The nanoparticles are usually of spherical shape.

The definition of PdI according to Malvern (referring to the ISO 13321:1996 norm) is based on the cumulants analysis that is performed to fit the correlation function: $Ln(C(tau))=a+b*tau+c*tau^2$, a third order fit where $PdI=2c/b^2$.

Zeta Potential

The zeta potential (ZP) of the nanoparticle is generally positive or at least neutral, preferably from about 0 to 50, preferably about 1 to 40, most preferably 5 to 30 mV. The average particle size (Z-Ave), the particle size distribution (PDI) and the zeta potential (ZP) may be measured with a Zetasizer Nano ZS instrument (Malvern, laser: $\lambda=532$ nm) with the Smoluchowski approximation.

The nanoparticle may be characterized in that the bio-resorbable polyester is a polylactic acid, a polyglycolic acid, a poly-caprolactone, a lactic acid-glycolic acid copolymer, a poly(lactic acid-co-glycolic acid)-poly(ethylene glycol) block copolymer, a lactic acid-glycolic acid-caprolactone terpolymer, a lactic acid-caprolactone copolymer, a poly dioxanone or a lactic acid-trimethylene carbonate copolymer or any blend of the afore mentioned polymers.

The nanoparticle may be characterized in that the bio-resorbable polyester without a hydrophilic polymer portion comprises a poly(D,L-lactide-co-glycolide).

The nanoparticle may be characterized in that the proportion of D,L-lactide to glycolide in the poly(D,L-lactide-co-glycolide) copolymer is from 70:30 to 30:70, preferably from 60:40 to 40:60, most preferred from 55:45 to 45:55 parts per mol.

The nanoparticle may be characterized in that, the bio-resorbable polyester without a hydrophilic polymer portion or with a polymeric portion has an inherent viscosity IV from 0.1 to 0.5, preferably from 0.1 to 0.3 or from 0.35 to 0.5 dL/g.

The nanoparticle may be characterized in that the hydrophilic polymer or the hydrophilic polymer portion is a polyethylene glycol.

The nanoparticle may be characterized in that the bio-resorbable polyester with a hydrophilic polymer portion comprises a poly(lactic acid-co-glycolic acid)-poly(ethylene glycol) block copolymer with the block structure AB, BA or ABA, wherein A is poly(lactic acid-co-glycolic acid) and B is poly(ethylene glycol) and wherein the poly(ethylene glycol) block comprises from about 0.1 to 25, preferably from 10 to 20% by weight of the block copolymer.

The nanoparticle may be characterized in that the bio-resorbable polyester and the hydrophilic polymer portion are comprised in a mixture of a poly(D,L-lactide-co-glycolide) copolymer with a proportion of D,L-lactide to glycolide from 60:40 to 40:60, preferably 55:45 to 45:55 parts per mol and a poly(D,L-lactic acid-co-glycolic acid)-poly(ethylene glycol) AB block copolymer with a proportion of D,L-lactide to glycolide from 60:40 to 40:60, preferably 55:45 to 45:55 parts per mol, wherein A is poly(D,L-lactic acid-co-glycolic acid) and B is poly(ethylene glycol) and wherein the poly(ethylene glycol) block comprises from about 10 to 20% by weight of the block copolymer.

The nanoparticle may be characterized in that the ratio by weight of the poly(D,L-lactide-co-glycolide) copolymer to the weight of the poly(D,L-lactic acid-co-glycolic acid)-poly(ethylene glycol) AB block copolymer is from 60:40 to 99.9:0.1, preferably from 80:20 to 99.8:0.2 most preferably from 95:5 to 99.5:0.5.

The nanoparticle may be characterized in that at least two cysteine residues are present in the amino acid sequence of the human lactoferrin-derived peptide.

The nanoparticle may be characterized in that the amino acid sequence of the human lactoferrin-derived peptide has a length of 14 to 30, preferably 18 to 26, most preferred of 20 to 24 amino acids.

The nanoparticle may be characterized in that a biologically active ingredient is comprised.

The nanoparticle may be characterized in that the biologically active ingredient is selected from the groups of analgesics, antibiotics or anti-infectives, antibodies, antiepileptics, antigens from plants, antirheumatics, betablocker, benzimidazole derivatives, beta-blocker, cardiovascular drugs, chemotherapeutics, CNS drugs, *digitalis* glycosides, gastrointestinal drugs, e.g. proton pump inhibitors, enzymes, hormones, liquid or solid natural extracts, mineral nutrients, nucleic acids, oligonucleotides, peptides, hormones, proteins, peptides, proteins, trace elements, urological drugs, vitamins and vaccines or from any mixtures thereof.

The nanoparticle may be characterized in that it is comprising a diagnostic marker.

The nanoparticle may be characterized in that the bio-resorbable polyester is a PLGA which is a poly(D,L-lactide-co-glycolide).

The nanoparticle may be characterized in that the proportion of D,L-lactide to glycolide in the poly(D,L-lactide-co-glycolide) copolymer is from 70:30 to 30:70, preferably from 60:40 to 40:60, most preferred from 55:45 to 45:55 parts per mol.

The nanoparticle may be characterized, in that the bio-resorbable polyester has an inherent viscosity IV from 0.1 to 0.5, preferably from 0.1 to 0.3 or from 0.3 to 0.5 dL/g.

The nanoparticle may be characterized in that wherein the bio-resorbable polyester without a hydrophilic polymer portion is a polylactic acid, a polyglycolic acid, a poly-caprolactone, a lactic acid-glycolic acid copolymer, a lactic acid-glycolic acid-caprolactone terpolymer, a lactic acid-caprolactone copolymer, a poly dioxanone or a lactic acid-trimethylene carbonate copolymer or any blend of the afore mentioned polymers.

The nanoparticle may be characterized in that, wherein the bio-resorbable polyester is mixture of a poly(D,L-lactide-co-glycolide) copolymer and a poly(D,L-lactic acid-co-glycolic acid)-poly(ethylene glycol) AB block copolymer with a proportion of D,L-lactide to glycolide from 60:40 to 40:60, preferably 55:45 to 45:55 parts per mol, wherein A is poly(D,L-lactic acid-co-glycolic acid) and B is poly(ethylene glycol) and wherein the poly(ethylene glycol) block comprises from about 10 to 20% by weight of the block copolymer.

The nanoparticle may be characterized in that the ratio by weight of the poly(D,L-lactide-co-glycolide) copolymer to the poly(D,L-lactic acid-co-glycolic acid)-poly(ethylene glycol) AB block copolymer is from 60:40 to 99:1, preferably from 80:98 to 98:2, most preferably from 85:15 to 95:5.

The nanoparticle may be characterized in that at least two cysteine residues are present in the amino acid sequence of the human lactoferrin-derived peptide.

The nanoparticle may be characterized in that the amino acid sequence of the human lactoferrin-derived peptide has a length of 14 to 30, preferably 18 to 26, most preferred of 20 to 24 amino acids.

The nanoparticle may be characterized in that a biologically active ingredient is comprised.

The nanoparticle may be characterized in that the biologically active ingredient is a DNA or a RNA.

The nanoparticle may be characterized in that a diagnostic marker is comprised.

A nanoparticle as disclosed may be prepared by emulsion techniques, for instance by emulsion solvent evaporation or extraction or precipitation. A nanoparticle as disclosed may be prepared by precipitation techniques. A double emulsion may be created with water-in-oil droplets preferably comprising a biologically active ingredient or a diagnostic marker in the water phase and the bio-resorbable polyester in the oil phase. With a second excessive phase of water that may include a stabilizer, water-in-oil-in-water droplets may be created. The nanoparticle core may then be coated with the C16-acylated human lactoferrin-derived peptide, which adsorbs on the surface of the core.

The nanoparticles as disclosed may further comprise pharmaceutically acceptable excipients in the core or onto the core. For instance, the nanoparticle may have an inner calcium phosphate structure. Such a nanoparticle structure is known from WO2015/181138A1. Other excipients in the core may be poly-L-lysine or polyethylene imine.

Relative Fluorescence with A549 (Human Lung Carcinoma) Cells

The nanoparticles as disclosed, comprising 50% by weight $C_{16}$-acetylated human lactoferrin-derived peptide and Lumogen F305 as fluorescence marker show a relative fluorescence per 100 A549 human lung carcinoma cells in flow cytometry, which is five-times or more or ten-times or more than the relative fluorescence of a comparable nanoparticle comprising a C2-acylated human lactoferrin-derived peptide instead of the $C_{16}$-acetylated human lactoferrin-derived peptide.

The nanoparticles as disclosed, comprising a bio-resorbable polyester and a hydrophilic polymer, comprising 50% by weight $C_{16}$-acetylated human lactoferrin-derived peptide and Lumogen F305 as fluorescence marker show a relative fluorescence per 100 A549 human lung carcinoma cells in flow cytometry, which is three times or more than the relative fluorescence of a comparable nanoparticle comprising the same bio-resorbable polyester but no hydrophilic polymer.

The relative fluorescence may be calculated as $$\frac{\text{Total counts}}{X \text{ Median}} * 100$$

A suitable measurement and calculation procedure may be as follows: A living A549 cell population of the unstained negative control may be gated and set as Lumogen F305 Red-negative cells. A histogram is set up for every measured sample with the relative fluorescence on the x-axis and the number of living cells on the y-axis. The Median of the x-axis represents the fluorescence intensity of the living cell population and therefore the amount of nanoparticle association and cell uptake. Due to the difference in cell counts the relative fluorescence was calculated per 100 cells.

$$\frac{\text{Total counts}}{X \text{ Median}} * 100$$

Bio-Resorbable Polyester

The nanoparticle comprises a core comprising a bio-resorbable polyester and a hydrophilic polymer. The hydrophilic polymer may be a covalently bound to the bio-resorbable polyester as a hydrophilic portion of the polymer or may be present as a separate polymer. Thus, the bio-resorbable polyester may be a bio-resorbable polyester with or without a hydrophilic polymer portion. A bio-resorbable polyester with a hydrophilic polymer portion is understand as a bio-resorbable polyester and a hydrophilic polymer or as a bio-resorbable polyester comprising hydrophilic polymer.

The bio-resorbable polyester is usually a hydrophobic polymer. A bio-resorbable polyester in the sense of the invention is preferably a lactic acid polymer or a lactic acid based polymer in a broad sense, for instance a homopolymer or copolymer based for instance on lactide (L-lactide, D-lactide, DL-lactide, mesolactide), glycolide, epsilon caprolactone, dioxanone, trimethylene carbonate, delta-valerolactone, gamma-butyrolactone and similar polymerizable heterocycles. These polymers can either be composed of one or else of a plurality of different monomer modules in the polymer chain such as for instance ethylene glycol. Bio-resorbable polyesters are raw materials which are widely used for the production of bio-resorbable surgical implants and also as a pharmaceutical carrier for the formulation of parenteral release systems.

The bio-resorbable polyester is preferably selected from lactic acid polymers or copolymers synthesized from monomer components or from a mixture of monomer components selected from the group consisting of a) to l):
a) D and L-lactide,
b) L lactide and glycolide,
c) D,L-lactide and glycolide,
d) L-lactide and epsilon-caprolactone,
e) L-lactide and dioxanone,
f) L-lactide and trimethylene carbonate,
g) L-lactide, D-lactide, meso-lactide or D,L-lactide,
h) L-lactide,
i) DL-lactide,
j) statistically distributed monomer units of L-lactide, D-lactide, meso-lactide or DL-lactide and epsilon caprolactone,
k) statistically distributed monomer units of L-lactide, D-lactide, meso-lactide or DL-lactide and dioxanone,
l) statistically distributed monomer units of L-lactide, D-lactide, meso-lactide or DL-lactide and trimethylene carbonate.

A bio-resorbable polyester without a hydrophilic polymer portion may be a polylactic acid, a polyglycolic acid, a poly-caprolactone, a lactic acid-glycolic acid copolymer, a lactic acid-glycolic acid-caprolactone polymer, a lactic acid-caprolactone copolymer, a poly-dioxanone or a lactic acid-trimethylene carbonate copolymer or any blend of the afore mentioned polymers.

Preferably a bio-resorbable polyester without a hydrophilic polymer portion may be a poly(D,L-lactide-co-glycolide) copolymer preferably with an inherent viscosity IV from 0.1 to 2.0, 0.12 to 1.2, 0.14 to 1.0, 0.16 to 0.44, 0.16 to 0.24 [dL/g] (The inherent viscosity IV may be measured at 0.1% w/v in $CHCl_3$ at 25° C. with an Ubbelhode size 0c glass capillary viscometer).

A suitable bio-resorbable polyester without a hydrophilic polymer portion may be a poly(D,L-lactide-co-glycolide) copolymer (PLGA) wherein the proportion of D,L-lactide to glycolide in the poly(D,L-lactide-co-glycolide) copolymer is from 80:20 to 20:80, 70:30 to 30:70, 60:40 to 40:60 parts per mol The inherent viscosity (IV) may be in the range from 0.1-0.5 or 0.12-0.45 (The Inherent viscosity may be measured at 0.1% w/v in $CHCl_3$ at 25° C. with an Ubbelhode size 0c glass capillary viscometer).

A suitable bio-resorbable polyester without a hydrophilic polymer portion may be RESOMER® RG 503 or RESOMER® RG 503 H which are a poly(D,L-lactide-co-glycolide/50:50 copolymers with an inherent viscosity IV from 0.16-0.44 or 0.16-0.24 [dL/g].

Another suitable bio-resorbable polyester without a hydrophilic polymer portion is RESOMER® RG 502 or RESOMER® RG 502 H which are a poly(D,L-lactide-co-glycolide/50:50 (mol %)) copolymers with an inherent viscosity IV from 0.16-0.44 or 0.16-0.24 [dL/g].

A bio-resorbable polyester with a hydrophilic polymer portion may be a poly(lactic acid-co-glycolic acid)-poly (ethylene glycol) block copolymer with the block structure AB, BA or ABA (PLGA-PEG, PEG-PLGA or PLGA-PEG-PLGA), wherein A is poly(lactic acid-co-glycolic acid) and B is poly(ethylene glycol) and wherein the poly(ethylene glycol) block comprises from about 0.1 to 40 0.1 to 25, 0.5 to 4, preferably from 10 to 20% by weight of the block copolymer.

A suitable corresponding commercially available PLGA-PEG AB-block copolymer with about 15% by weight PEG content is for instance RESOMER® RGP d 50155 or RESOMER® Select 5050 DLG mPEG 5000.

A most preferred combination of a bio-resorbable polyester without a hydrophilic polymer portion and a bio-resorbable polyester with a hydrophilic polymer portion is a mixture of a poly(D,L-lactide-co-glycolide) copolymer with a proportion of D,L-lactide to glycolide from 60:40 to 40:60, preferably 55:45 to 45:55 parts per mol and a poly(D,L-lactic acid-co-glycolic acid)-poly(ethylene glycol) AB-block copolymer with a proportion of D,L-lactide to glycolide from 60:40 to 40:60, preferably 55:45 to 45:55 parts per mol, wherein A is poly(D,L-lactic acid-co-glycolic acid) and B is poly(ethylene glycol) and wherein the poly (ethylene glycol) block comprises from about 10 to 20% by weight of the block-copolymer (PLGA/PLGA-PEG). Preferably the ratio by weight of the poly(D,L-lactide-co-glycolide) copolymer to the poly(D,L-lactic acid-co-glycolic acid)-poly(ethylene glycol) AB block copolymer in the mixture is from 60:40 to 99:1, preferably from 80:20 to 98:2, most preferably from 85:15 to 95:5.

The term "bio-resorbable" in "bio-resorbable polyester" means that the polyester, which is preferably a lactic acid based polymer, is after implantation or injection in the human body or in the body of an animal in contact with the body fluids broken down into oligomers in a slow hydrolytic reaction. Hydrolysis end-products such as lactic acid or glycolic acid are metabolized into carbon dioxide and water. Other exchangeable expressions for the term "bio-resorbable polyester" which are often used are "resorbable polyester", "bio-degradable polyester" or "adsorptive polyester".

These kind of bio-resorbable polyester or biodegradable polyester polymers are generally well known in the art, for example from EP1468035, U.S. Pat. No. 6,706,854, WO2007/009919A2, EP1907023A, EP2263707A, EP2147036, EP0427185 or U.S. Pat. No. 5,610,266. Depending on the production-process the polymers may have different end groups such as ester or acid end groups.

Hydrophilic Polymer

The nanoparticle comprises a core comprising a bio-resorbable polyester and a hydrophilic polymer. The hydrophilic polymer may be a covalently bound to the bio-resorbable polyester as a hydrophilic portion of the polymer or may be present as a separate polymer. A hydrophilic polymer may be defined as a polymer, which is water-soluble or water-swellable over a broad pH range from at least pH 3 to pH 10 at 25° C. Preferably, the hydrophilic polymer is a linear polymer. Preferably, the hydrophilic polymer is not cross-linked.

The hydrophilic polymer, present as separate polymer or as a hydrophilic polymer portion as part of the bio-resorbable polymer, is preferably a polyethylene glycol (PEG). Polyethylene glycols of the types ranging from PEG 300, PEG 1000, PEG 2000, PEG 4000, PEG 5000 up to PEG 10.000 or PEG 20.000 may be suitable. Synonyms to polyethylene glycol (PEG) are polyethylenoxide (PEO) or polyoxyethylene (POE). The term PEG is often used for polymers with lower molecular mass, e.g. 20,000 g/mol or less. The term PEO is often used for polymers with higher molecular masses such as 20,000 g/mol or more.

C16-Monoacylated Human Lactoferrin-Derived Peptide (C16-hLFF)

The nanoparticle is comprising a core, comprising a bio-resorbable polyester and a hydrophilic polymer, wherein the hydrophilic polymer is a portion of the bio-resorbable polyester or a separate polymer, and, onto the core, an acylated human lactoferrin-derived peptide. "Onto the core" shall mean that the acylated human lactoferrin-derived peptide is present on the surface of the core, respectively coated onto the core or absorbed on the surface of the core. The coating or absorption of the acylated human lactoferrin-derived peptide onto the core is preferably a result of non-covalent interaction.

The $C_{16}$-monoacylated human lactoferrin-derived peptide is a peptide with the amino acid sequence SEQ ID No. 1: KCFQWQRNMRKVRGPPVSCIKR or an amino acid sequence, which does not differ in more than 8 amino acid positions from the sequence SEQ. ID. No. 1, wherein the peptide is acylated or substituted with a $C_{16}$-monoacyl group (palmitoyl group) at the N-terminus of the peptide (the $NH_2$-group of the amino acid backbone). To give an example, in the case of the sequence SEQ ID No. 1: KCFQWQRNMRKVRGPPVSCIKR, the N-terminus is the $NH_2$-group of the amino acid backbone of the first amino acid "K" (lysine) and the C-terminus is the COOH-group of the amino acid backbone of the last amino acid "R" (arginine). Due to chemical synthesis, the $C_{16}$-monoacylated human lactoferrin-derived peptide may be present in the form of a C-terminal amide (—$CONH_2$).

In the nanoparticle, the amount of the acylated human lactoferrin-derived peptide to the bio-resorbable polyester and the hydrophilic polymer is about 1 to 100% by weight or 5 to 75% by weight, preferably about 25 to 75% by weight.

The human lactoferrin-derived peptide with the amino acid sequence SEQ ID No. 1: KCFQWQRNMRKVRGPPVSCIKR or a peptide with an amino acid sequence, which does not differ in more than 8 amino acid positions from the sequence SEQ. ID. No. 1, is preferably chemically synthesized from the single amino acids as well known in the art. Acylation of the human lactoferrin-derived peptide may be performed by standard chemical acylation of the peptide with a corresponding $C_{16}$-monoacyl molecule. Standard chemical acylation techniques are well-known to a skilled person. Corresponding $C_{16}$-acylated human lactoferrin-derived peptides are also commercially available on demand.

The human lactoferrin-derived peptide used for $C_{16}$-acylation is a peptide with the amino acid sequence SEQ ID No. 1: KCFQWQRNMRKVRGPPVSCIKR or a peptide with an amino acid sequence, which does not differ in more than 8, 7, 6, 5, 4, 3, 2 or 1 amino acid positions from the sequence SEQ. ID. No. 1.

The human lactoferrin-derived peptide to be C16-monoacylated may have a length of 14 to 30, 19 to 28, 20 to 25, 21 to 23 or most preferred 22 amino acids. Preferably, the amino acid sequence of the human lactoferrin-derived peptide may include two or more or exactly two cysteine residues. Preferably, the amino acid sequence of the human lactoferrin-derived peptide may include at least two cysteine residues that may form an internal cysteine-cysteine-bridge (cystine-bridge). Preferably, two cysteine residues are present in oxidized form, forming an internal cystine-bridge. Preferably the two cysteine residues correspond to the positions 2 and 19 of the peptide sequence SEQ ID NO: 1 or of an amino acid sequence, which does not differ by more than 8 amino acid positions from the sequence SEQ ID NO: 1.

The human lactoferrin-derived peptide to be acylated, is a peptide with the amino acid sequence SEQ ID No. 1 KCFQWQRNMRKVRGPPVSCIKR or a peptide with an amino acid sequence, which does not differ in more than 8, 7, 6, 5, 4, 3, 2 or 1 amino acid positions from the sequence SEQ. ID. No. 1 may be preferably prepared or made available by chemical synthesis. In this case the peptide with the amino acid sequence SEQ ID No. 1 KCFQWQRNMRKVRGPPVSCIKR or the amino acid sequence, which does not differ in more than 8, 7, 6, 5, 4, 3, 2 or 1 amino acid positions from the sequence SEQ. ID. No. 1, may be synthesized as C-terminal amides and/or with an N-terminal acetyl-group.

The term "differ in an amino acid position" shall be understood in the sense that there is, compared to the sequence SEQ. ID. No. 1, a different amino acid present in a certain position or there is no amino acid in a certain position or there is an additional amino acid present within the sequence or added to the sequence or any combination of these cases.

Most preferably, the human lactoferrin-derived peptide comprised in the acylated peptide does not differ in more than 8, 7, 6, 5, 4, 3, 2 or 1 amino acid positions from the sequence SEQ ID NO: 1 SEQ. ID. No. 1 whereby at least two cysteine residues are present. Preferably the two cysteine according to positions 2 and 19 of SEQ ID NO: 1 are present. Preferably, the cysteine residues are present in oxidized form, forming an internal cysteine-cysteine-bridge (cystine-bridge). For efficient disulfide bridge formation, the peptides may be dissolved in 50 mM Hepes buffer pH 8 at a concentration of 2 mM and oxidized for 2 h at 37° C. (Wallbrecher et al., Cell Mol Life Sci. 2014 July; 71(14): 2717-29).

The human lactoferrin-derived peptide may be synthesized as C-terminal amide using solid-phase peptide synthesis (EMC microcollections). For efficient disulfide bridge formation, the peptides were may be dissolved in 50 mM Hepes buffer pH 8 at a concentration of 2 mM and oxidized for 2 h at 37° C. (Wallbrecher et al., Cell Mol Life Sci. 2014 July; 71(14):2717-29).

Biologically Active Ingredients

The nanoparticle may comprise one or more biologically active ingredients.

The term "biologically active agent" is used herein to include a compound of interest contained in or on a pharmaceutical formulation or dosage form that is used for pharmaceutical or medicinal purposes to provide some form of therapeutic effect or elicit some type of biologic response or activity.

A biologically active ingredient in the sense of the present application is a substance that may be delivered to a mammalian or human body in order to achieve a therapeutic effect and/or to cure a disease. Preferably, the biologically active ingredient is water-soluble at 20° C.

The term "biologically active ingredient" may be used in the sense of "pharmaceutical active ingredient", which again has the same meaning as "active pharmaceutical ingredient (API)".

A human lactoferrin-derived peptide especially the C16-aclylated human lactoferrin-derived peptide as disclosed may be regarded as an excipient, for instance for balancing the zeta potential properties of the nanoparticle or for supporting the delivery of a biologically active ingredient into cells but is not regarded as a biologically active ingredient itself.

The invention is preferably useful for nanoparticles with improved cell delivery for biologically active ingredients with improved bioavailability or for the delivery diagnostic markers.

Therapeutic and chemical classes of the biologically active ingredients used in sustained release formulated coated pharmaceutical dosage forms are for instance analgesics, antibiotics or anti-infectives, antibodies, antiepileptics, antigens from plants, antirheumatics, betablocker, benzimidazole derivatives, beta-blocker, cardiovascular drugs, chemotherapeutics, CNS drugs, *digitalis* glycosides, gastrointestinal drugs, e.g. proton pump inhibitors, enzymes, hormones, liquid or solid natural extracts, nucleic acids, oligonucleotides, peptide hormone, proteins, therapeutic bacteria, peptides, proteins (metal)salt f.e. aspartates, chlorides, orothates, urology drugs, vitamins, trace elements, minerals or vaccines.

Examples of biologically active ingredients or pharmaceutically active may be: acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D-arginine-vasopressin, deramciclane, detirelix, dexlansoprazole, diclofenac, didanosine, digitoxin and other *digitalis* glycosides, dihydrostreptomycin, dimethicone, divalproex, drospirenone, duloxetine, enzymes, erythromycin, esomeprazole, estrogens, etoposide, exenatide, famotidine, fluorides, garlic oil, glucagon, GLP-1, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, olsalazine, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof.

The biologically active ingredient may be a "small molecule" or a peptide, which is different from the human lactoferrin-derived peptide. Examples for suitable peptides are for instance peptide hormones such as a human growth hormone. The biologically active ingredient may be a protein. Examples for suitable proteins are for instance antibodies, interleukins, interferons or protein based vaccines.

The biologically active ingredient may be a nucleic acid, such as DNA or RNA. The DNA or RNA may be a double-stranded or single-stranded. DNA may be plasmid DNA (pDNA).

The pharmaceutical active ingredient may be a siRNA (small interfering RNA).

The term "siRNA" is well known to a person skilled in the art. A typical siRNA may be defined as a double stranded RNA of about 19-23 base pairs length, in which single strands may overlap at the 3'-end for two nucleotides. siRNAs are cleavage products from large double-stranded RNAs such as cellular mRNA or RNA generated from viruses during their replication in living cells. These types of RNAs may be cut down to siRNAs for instance by the enzyme "Dicer", which is a type III RNase. siRNAs play an important role in post-transcriptional gene-silencing processes. Longer siRNAs, for instance 60 base pairs or longer, may also be synthesized by means of expression-vectors. Therefore siRNAs are of high interest to be used as active ingredients in order to achieve certain therapeutic effects and/or to cure certain diseases.

Further examples for biologically or active pharmaceutically ingredients are:

Pharmaceutically active substances may belong to one or more active ingredient classes such as ACE inhibitors, adrenergics, adrenocorticosteroids, acne therapeutic agents, aldose reductase inhibitors, aldosterone antagonists, alpha-glucosidase inhibitors, alpha 1 antagonists, remedies for alcohol abuse, amino acids, amoebicides, anabolics, analeptics, anaesthetic additions, anaesthetics (non-inhalational), anaesthetics (local), analgesics, androgens, angina therapeutic agents, antagonists, antiallergics, antiallergics such as PDE inhibitors, antiallergics for asthma treatment, further antiallergics (e.g. leukotriene antagonists, antianaemics, antiandrogens, antianxiolytics, antiarthritics, antiarrhythmics, antiatheriosclerotics, antibiotics, anticholinergics, anticonvulsants, antidepressants, antidiabetics, antidiarrhoeals, antidiuretics, antidotes, antiemetics, antiepileptics, antifibrinolytics, antiepileptics, antihelmintics, antihistamines, antihypotensives, antihypertensives, antihypertensives, antihypotensives, anticoagulants, antimycotics, antiestrogens, antiestrogens (non-steroidal), antiparkinson agents, antiinflammatory agents, antiproliferative active ingredients, antiprotozoal active ingredients, antirheumatics, antischistosomicides, antispasmolytics, antithrombotics, antitussives, appetite suppressants, arteriosclerosis remedies, bacteriostatics, beta-blockers, beta-receptor blockers, bronchodilators, carbonic anhydrase inhibitors, chemotherapeutic agents, choleretics, cholinergics, cholinergic agonists, cholinesterase inhibitors, agents for the treatment of ulcerative colitis, cyclooxygenaze inhibitors diuretics, ectoparasiticides, emetics, enzymes, enzyme inhibitors, enzyme inhibitors, active ingredients to counter vomiting, fibrinolytics, fungistatics, gout remedies, glaucoma therapeutic agents, glucocorticoids, glucocorticosteroids, haemo, statics, cardiac glycosides, histamine H2 antagonists, hormones and their inhibitors, immunotherapeutic agents, cardiotonics, coccidiostats, laxatives, lipid-lowering agents, gastrointestinal therapeutic agents, malaria therapeutic agents, migraine remedies, microbiocides, Crohn's disease, metastasis inhibitors, migraine remedies, mineral preparations, motility-increasing active ingredients, muscle relaxants, neuroleptics, active ingredients for treatment of estrogens, osteoporosis, otologicals, antiparkinson agents, phytopharmaceuticals, proton pump inhibitors, prostaglandins, active ingredients for treating benign prostate hyperblasia, active ingredients for treating pruritus, psoriasis active ingredients, psychoactive drugs, free-radical scavengers, renin antagonists, thyroid therapeutic agents, active ingredients for treating seborrhoea, active ingredients to counter seasickness, spasmolytics, alpha- and beta-sympathomimetics, platelet aggregation inhibitors, tranquilizers, ulcer therapeutic agents, further ulcer therapeutic agents, agents for the treatment of urolithiasis, virustatics, vitamins, cytokines, active ingredients for combination therapy with cytostatics, cytostatics.

Examples of suitable active components are acarbose, acetylsalicylic acid, abacavir, aceclofenac, aclarubicin, acyclovir, actinomycin, adalimumab, adefovir, adefovirdipivoxil, adenosylmethionine, adrenaline and adrenaline derivatives, agalsidase alpha, agalsidase beta, alemtuzumab, almotriptan, alphacept, allopurinol, almotriptan, alosetron, alprostadil, amantadine, ambroxol, amisulpride, amlodipine, amoxicillin, 5 aminosalicylic acid, amitriptyline, amlodipine, amoxicillin, amprenavir, anakinra, anastrozole, androgen and androgen derivatives, apomorphine, aripiprazole, arsenic trioxide, artemether, atenolol, atorvastatin, atosiban, azathioprine, azelaic acid, barbituric acid derivatives, balsalazide, basiliximab, beclapermin, beclomethasone, bemiparin, benzodiazepines, betahistine, bexaroten, bezafibrate, bicalutamide, bimatoprost, bosentan, botulinus toxim, brimonidine, brinzolamide, budesonide, budipine, bufexamac, bumetanide, buprenorphine, bupropion, butizine, calcitonin, calcium antagonists, calcium salts, candesartan, capecitabine, captopril, carbamazepine, carifenacin, carvedilol, caspofungin, cefaclor, cefadroxil, cefalexin cefalosporins, cefditoren, cefprozil, celecoxib, cepecitabine, cerivastatim, cetirizine, cetrorelix, cetuximab, chenodeoxycholic acid, chorionic gonadotropin, ciclosporin, cidofovir, cimetidine, ciprofloxacin, cisplatin, cladribine, clarithromycin, clavulanic acid, clindamycin, clobutinol, clonidine, clopidogrel, codeine, caffeine, colestyramine, cromoglicic acid, cotrimoxazole, coumarin and coumarin derivatives, darbepoetin, cysteamine, cysteine, cytarabine, cyclophosphamide, cyproterone, cytarabine, daclizumab, dalfopristin, danaparoid, dapiprazole, darbepoetin, defepripone, desipramine, desirudin, desloaratadine, desmopressin, desogestrel, desonide, dexibuprofen, dexketoprofen, disoproxil, diazepam and diazepam derivatives, dihydralazine, diltiazem, dimenhydrinate, dimethyl sulphoxide, dimeticon, dipivoxil, dipyridarnoi, dolasetron, domperidone, and domperidane derivatives, donepzil, dopamine, doxazosin, doxorubizin, doxylamine, diclofenac, divalproex, dronabinol, drospirenone, drotrecogin alpha, dutasteride, ebastine, econazole, efavirenz, eletripan, emidastine, emtricitabine, enalapril, encepur, entacapone, enfurvirtide, ephedrine, epinephrine, eplerenone, epoetin and epoetin derivatives, eprosartan, eptifibatide, ertapenem, esomeprazole, estrogen and estrogen derivatives, etanercept, ethenzamide, ethinestradiol, etofenamate, etofibrate, etofylline, etonogestrel, etoposide, exemestan, exenatide, exetimib, famciclovir, famotidine, faropenan daloxate, felodipine, fenofibrate, fentanyl, fenticonazole, fexofenadine, finasteride, fluconazole, fludarabine, flunarizine, fluorouracil, fluoxetine, flurbiprofen, flupirtine, flutamide, fluvastatin, follitropin, fomivirsen, fondaparinux, formoterol, fosfomicin, frovatriptan, furosemide, fusidic acid, gadobenate, galantamine, gallopamil, ganciclovir, ganirelix, gatifloxacin, gefitinib, gemfibrozil, gentamicin, gepirone, GLP-1, progestogen and progestogen derivatives, ginkgo, glatiramer, glibenclamide, glipizide, glucagon, glucitol and glucitol derivatives, glucosamine and glucosamine derivatives, glycoside antibiotics, glutathione, glycerol and glycerol derivatives, hypothalamus hormones, goserelin, grepafloxacin, gyrase inhibitors, guanethidine, gyrase inhibitors, haemin, halofantrine, haloperidol, urea derivatives as oral antidiabetics, heparin and heparin derivatives, cardiac glycosides, hyaluronic acid, hydralazine, hydrochlorothiazide and hydrochloro, thiazide derivatives, hydroxyomeprazole, hydroxyzine, ibritumomab, ibuprofen, idarubicin, ifliximab, ifosfamide, iloprost, imatinib, imidapril, imiglucerase, imipramine, imiquimod, imidapril, indometacin, indoramine, infliximab, insulin, insulin glargin, interferons, irbesartan, irinotecan, isoconazole, isoprenaline, itraconazole, ivabradines, iodine and iodine derivatives, St. John's wort, potassium salts, ketoconazole, ketoprofen, ketotifen, lacidipine, lansoprazole, laronidase, latanoprost, leflunomide, lepirudin, lercanidipine, leteprinim, letrozole, levacetylmethadol, levetiracetam, levocetirizine, levodopa, levodrpropicin, levomethadone, licofelone, linezolide, lipinavir, lipoic acid and lipoic acid derivatives, lisinopril, lisuride, lofepramine, lodoxamide, lomefloxacin, lomustine, loperamide, lopinavir, loratadine, lornoxicam, losartan, lumefantrine, lutropine, magnesium salts, macrolide antibiotics, mangafodipir, maprotiline, mebendazole, mebeverine, meclozine, mefenamic acid, mefloquine, meloxicam, memantine, mepindolol, meprobamate, meropenem, mesalazine, mesuximide, metamizole, metformin, methadone, methotrexate, methyl 5-amino-4-oxopentanoate, methylnaloxone, methylnaloxone, methylaltrexones, methylphenidate, methylprednisolone, metixen, metoclopramide, metoprolol, metronidazole, mianserin, mibefradil, miconazole, mifepristone, miglitol, miglustad, minocycline, minoxidil, misoprostol, mitomycin, mizolastine, modafinil, moexipril, montelukast, moroctocog, morphinans, morphine and morphine derivatives, moxifloxacin, ergot alkaloids, nalbuphine, naloxone, naproxen, naratriptan, narcotine, natamycin, nateglinide, nebivolol, nefazodone, nelfinavir, neostigmine, neramexan, nevirapine, nicergoline, nicethamide, nifedipine, niflumic acid, nimodipine, nimorazole, nimustine, nesiritide, nisoldipine, norfloxacin, novamine sulphone, noscapine, nystatin, ofloxacin, oktotride, olanzapine, olmesartan, olsalazine, oseltamivir, omeprazole, omoconazole, ondansetron, orlistat, oseltamivir, oxaceprol, oxacillin, oxaliplatin, oxaprozin, oxcarbacepin, oxicodone, oxiconazole, oxymetazoline, palivizumab, palanosetron, pantoprazole, paracetamol, parecoxib, paroxetine, pegaspargase, peginterferon, pegfilgrastrim, penciclovir, oral penicillins, pentazocine, pentifylline, pentoxifylline, peptide antibiotics, perindopril, perphenazine, pethidine, plant extracts, phenazone, pheniramine, phenylbutyric acid, phenytoin, phenothiazines, phenserine, phenylbutazone, phenytoin, pimecrolimus, pimozide, pindolol, pioglitazone, piperazine, piracetam, pirenzepine, piribedil, pirlindol, piroxicam, pramipexol, pramlintide, pravastatin, prazosin, procaine, promazine, propiverine, propranolol, propionic acid derivatives, propyphenazone, prostaglandins, protionamide, proxyphylline, quetiapine, quinapril, quinaprilate, quinupristine, ramipril, ranitidine, rabeprazole, raloxifen, ranolazine, rasburicase, reboxetin, repaclinides, reproterol, reserpine, revofloxacin, ribavirin, rifampicin, riluzoles, rimexolone, risedronate, risperidone, ritonavir, rituximab, rivastimen, risatriptan, rofecoxib, ropinirol, ropivacaine, rosiglitazone, roxatidine, roxithromycin, ruscogenin, rosuvastatin, rutoside and rutoside derivatives, sabadilla, salbutamol, salicylates, salmeterol, saperconazoles, thyroid hormones, scopolamine, selegiline, sertaconazole, sertindole, sertraline, sevelamer, sibutramine, sildenafil, silicates, simvastatin, sirolimus, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulphasalazine, sulpiride, sultamicillin, sultiam, sumatriptan, suxamethonium chloride, tacrine, tacrolimus, tadalafil, taliolol, talsaclidine, tamoxifen, tasonermin, tazarotene, tegafur, tegaserod, telithromycin, telmisartan, temoporfin, temozolomide, tenatoprazole, tenecteplase, teniposide, tenofovir, tenoxicam, teriparatide, terazosin, terbinafine, terbutaline, terfenadine, teriparatide, terlipressin, tertatolol, testosterone and testosterone derivatives, tetracyclines, tetryzoline, tezosentan, theobromine, theophylline, theophylline derivatives, thiamazole, thiotepa, thr. growth factors, tiagabine, tiapride, tibolone, ticlopidine, tilidine, timolol, tinidazole, tioconazole, tioguanine, tiotropium, tioxolone, tirazetam, tiropramide, trofiban, tizanidine, tolazoline, tolbutamide, tolcapone, tolnaftate, tolperisone, tolterodine, topiramate, topotecan, torasemide, tramadol, tramazoline, trandolapril, tranylcypromine, trapidil, trastuzumab, travoprost, trazodone, trepostinil, triamcinolone and triamcinolone derivatives, triamterene, trifluperidol, trifluridine, trimetazidines, trimethoprim, trimipramine, tripelennamine, triprolidine, trifosfamide, tromantadine, trometamol, tropalpine, trovafloxacin, troxerutin, tulobuterol, trypsins, tyramine, tyrothricin, urapidil, ursodeoxycholic acid, theophylline ursodeoxycholic acid, valaciclovir, valdecoxib, valganciclovir, valproic acid, valsartan, vancomycin, vardenafil, vecuronium chloride, venlafaxine, verapamil, verteporfin, vidarabine, vigabatrine, viloxazine, vinblastine, vincamine, vincristine, vindesine, vinorelbine, vinpocetine, viquidil, vitamin D and derivatives of vitamin D, voriconazole, warfarin, xantinol nicotinate, ximelagatran, xipamide, zafirlukast, zalcitabine, zaleplon, zanamivir, zidovudine, ziprasidone, zoledronic acid, zolmitriptan, zolpidem, zoplicone, zotepine and the like.

The active components can, if desired, also be used in the form of their pharmaceutically acceptable salts or derivatives, and in the case of chiral active ingredients it is possible to employ both optically active isomers and racemates or mixtures of diastereomers. If desired, the compositions of the invention may also comprise two or more active pharmaceutical ingredients.

Diagnostic Markers

The nanoparticle as disclosed may comprise a diagnostic marker. The diagnostic marker may be a fluorescence marker such as for instance Fluoresceinamine®, Rhodamine®-B-ethylene-diamine or Lumogen® F305 or a radioactive marker as used in clinical diagnostics. The coupling of the marker to the nanoparticle may be covalently by chemical reaction or non-covalently (Fluoresceinamine®) by van-der-Waals forces (hydrogen-bridges) or by ionic interactions.

Dosage Form

Disclosed is a pharmaceutical dosage form comprising a multitude of nanoparticles comprising one or more biologically active ingredients or one or more diagnostic markers, wherein the dosage form comprises a pellet, a tablet, a capsule, a spray, an aerosol, a powder, a sachet, a suppository or an injection solution or dispersion.

The medicament in multilayer form as claimed in the present application makes primarily sense as multiparticulate pharmaceutical form. Thus a pharmaceutical dosage form comprising a multitude of the nanoparticles as described herein is disclosed, wherein the dosage form may comprise a pellet, a tablet, a capsule or an injection solution or dispersion.

The term pellet-containing tablet or compressed tablet is well known to a skilled person. Such a tablet may have a size of around 5 to 25 mm for instance. Usually, defined pluralities of small active ingredient containing pellets are compressed therein together with binding excipients to give the well-known tablet form. After oral ingestion and contact with the body fluid the tablet form is disrupted and the pellets are set free. The compressed tablet combines the advantage of the single dose form for ingestion with the advantages of a multiple forms, for instance the dosage accuracy.

The term minitablet is well known to the skilled person. A minitablet is smaller than the traditional tablet and may have a size of around 1 to 4 mm. The minitablet is, like a pellet, a single dosage form to be used in multiple dosages. In comparison to pellets, which may be in the same size, minitablets usually have the advantage of having more regular surfaces which can be coated more accurately and more uniformly. Minitablets may be provided enclosed in capsules, such as gelatine capsules. Such capsules disrupt after oral ingestion and contact with the gastric or intestinal fluids and the minitablets are set free. Another application of minitablets is the individual fine adjustment of the active ingredient dosage. In this case the patient may ingest a defined number of minitablets directly which matches to the severe of the decease to cure but also to his individual body weight. A minitablet is different from pellet-containing compressed tablet as discussed above.

The term sachet is well known to the skilled person. It refers to small sealed package which contains the active ingredient often in pellet containing liquid form or also in dry pellet or powder form. The sachet itself is only the package form is not intended to be ingested. The content of the sachet may be dissolved in water or as an advantageous feature may be soaked or ingested directly without further liquid. The latter is advantageous feature for the patient when the dosage form shall be ingested in a situation where no water is available. The sachet is an alternative dosage form to tablets, minitablets or capsules.

The term capsule is well known to the skilled person. A capsule is like the sachet a container for pellets containing liquids or also dry pellets or powders. However, in contrast to the sachet the capsule consists of pharmaceutically acceptable excipients such as gelatine or hydroxypropylmethylcellulose and is intended to be ingested like a tablet. The capsules disrupts after oral ingestion and contact with the gastric or intestinal fluids and the contained multiple units are set free. Capsules for pharmaceutical purposes are commercially available in different standardized sizes. For gastric resistance and controlled release in the small intestine or in the colon, capsules may be provided with an enteric coating, such as with anionic celluloses or with anionic (meth)acrylate copolymers (EUDRAGIT® L30 D. EUDRAGIT® L100-55, EUDRAGIT® S or EUDRAGIT® FS polymer types).

Use

The application further discloses the use of the nanoparticle in a method of preparing a pharmaceutical composition suitable for the oral or parenteral delivery of a biologically active ingredient or a diagnostic marker included in the nanoparticle.

A nanoparticle comprising a biologically active ingredient or a diagnostic marker as described herein is disclosed for use as a medicament or part of a medicament for the oral, pulmonal, nasal, buccal, vaginal or parenteral delivery of a biologically active ingredient or as a diagnostic marker.

Items

The invention is characterized by the following items:

Item 1: Nanoparticle comprising a core, comprising a bio-resorbable polyester and a hydrophilic polymer, wherein the hydrophilic polymer is a portion of the bio-resorbable polyester or a separate polymer, and, onto the core, an acylated human lactoferrin-derived peptide, wherein the acylated human lactoferrin-derived peptide is a peptide with the amino acid sequence SEQ ID No. 1: KCFQWQRNMRKVRGPPVSCIKR or an amino acid sequence, which does not differ by more than 8 amino acid positions from the sequence SEQ. ID. No. 1 and wherein the N-terminus of the human lactoferrin-derived peptide is acylated with a $C_{16}$-monoacyl group.

2. Nanoparticle according to item 1, wherein the bio-resorbable polyester and the hydrophilic polymer is
i) a bio-resorbable polyester without a hydrophilic polymer portion and a hydrophilic polymer or
ii) a bio-resorbable polyester with a hydrophilic polymer portion or
iii) a bio-resorbable polyester with a hydrophilic polymer portion and a hydrophilic polymer or
iv) a bio-resorbable polyester without a hydrophilic polymer portion, a hydrophilic polymer and a bio-resorbable polyester with a hydrophilic polymer portion.

3. Nanoparticle according to items 1 or 2, wherein the amount of the acylated human lactoferrin-derived peptide to the bio-resorbable polyester and the hydrophilic polymer is about 1 to 100% by weight or 5 to 75% by weight, preferably about 25 to 75% by weight.

4. Nanoparticle according to one or more of items 1 to 15, wherein the ratio by weight of the bio-resorbable polyester to hydrophilic polymer is from 60:40 to 99.9:0.1, preferably from 80:20 to 99.8:0.2, most preferably from 95:5 to 99.5:0.5.

5. Nanoparticle according to one or more of items 1 to 4, wherein the average particle size (Z-Ave) is in the range of about 50 to 900, preferably about 100 to 350, most preferably about 200 to 300 nm.

6. Nanoparticle according to one or more of items 1 to 5, wherein the particle size distribution (PDI) is in the range of less than 0.3 or from 0.05 to 0.3, 0.08 to 0.2 or 0.09 to 0.19.

7. Nanoparticle according to one or more of items 1 to 6, wherein the zeta potential of the nanoparticle is about 0 to 50, preferably about 1 to 40, most preferably 5 to 30 mV.

8. Nanoparticle according to one or more of items 1 to 7, wherein the bio-resorbable polyester without a hydrophilic polymer portion is a polylactic acid, a polyglycolic acid, a poly-caprolactone, a lactic acid-glycolic acid copolymer, a lactic acid-glycolic acid-caprolactone terpolymer, a lactic acid-caprolactone copolymer, a poly dioxanone or a lactic acid-trimethylene carbonate copolymer or any blend of the afore mentioned polymers.

9. Nanoparticle according to one or more of items 1 to 8, wherein the bio-resorbable polyester without a hydrophilic polymer portion comprises a poly(D,L-lactide-co-glycolide).

10. Nanoparticle according to item 9, wherein the proportion of D,L-lactide to glycolide in the poly(D,L-lactide-co-glycolide) copolymer is from 70:30 to 30:70, preferably from 60:40 to 40:60, most preferred from 55:45 to 45:55 parts per mol.

11. Nanoparticle according to one or more of items 1 to 10, wherein the bio-resorbable polyester without a hydrophilic polymer portion or with a polymeric portion has an inherent viscosity IV from 0.1 to 0.5, preferably from 0.1 to 0.3 or from 0.3 to 0.5 dL/g.

12. Nanoparticle according to one or more of items 1 to 11, wherein the hydrophilic polymer or the hydrophilic polymer portion is a polyethylene glycol.

13. Nanoparticle according to one or more of items 1 to 12, wherein the bio-resorbable polyester with a hydrophilic polymer portion comprises a poly(lactic acid-co-glycolic acid)-poly(ethylene glycol) block copolymer with the block structure AB, BA or ABA, wherein A is poly(lactic acid-co-glycolic acid) and B is poly(ethylene glycol) and wherein the poly(ethylene glycol) block comprises from about 0.1 to 40, 0.1 to 25 or 0.2 to 4, preferably from 10 to 20% by weight of the block copolymer.

14. Nanoparticle according to one or more of items 1 to 13, wherein the bio-resorbable polyester and the hydrophilic polymer portion are comprised in a mixture of a poly(D,L-lactide-co-glycolide) copolymer with a proportion of D,L-lactide to glycolide from 60:40 to 40:60, preferably 55:45 to 45:55 parts per mol and a poly(D,L-lactic acid-co-glycolic acid)-poly(ethylene glycol) AB block copolymer with a proportion of D,L-lactide to glycolide from 60:40 to 40:60, preferably 55:45 to 45:55 parts per mol, wherein A is poly(D,L-lactic acid-co-glycolic acid) and B is poly(ethylene glycol) and wherein the poly(ethylene glycol) block comprises from about 10 to 20% by weight of the block copolymer.

15. Nanoparticle according to Item 14, wherein the ratio by weight the of the poly(D,L-lactide-co-glycolide) copolymer to the weight of the poly(D,L-lactic acid-co-glycolic acid)-poly(ethylene glycol) AB block copolymer is from 60:40 to 99.9:0.1, preferably from 80:20 to 99.8:0.2 most preferably from 95:5 to 99.5:0.5.

16. Nanoparticle according to one or more of items 1 to 15, wherein at least two cysteine residues are present in the amino acid sequence of the human lactoferrin-derived peptide.

17. Nanoparticle according to one or more of items 1 to 16, wherein the amino acid sequence of the human lactoferrin-derived peptide has a length of 14 to 30, preferably 18 to 26, most preferred of 20 to 24 amino acids.

18. Nanoparticle according to one or more of items 1 to 17, wherein a biologically active ingredient is comprised.

19. Nanoparticle according to Item 18, wherein the biologically active ingredient is selected from the groups of analgesics, antibiotics or anti-infectives, antibodies, antiepileptics, antigens from plants, antirheumatics, betablocker, benzimidazole derivatives, beta-blocker, cardiovascular drugs, chemotherapeutics, CNS drugs, *digitalis* glycosides, gastrointestinal drugs, e.g. proton pump inhibitors, enzymes, hormones, liquid or solid natural extracts, nucleic acids, oligonucleotides, peptides, hormones, proteins, peptides, proteins, urological drugs, vaccines, vitamins, trace elements, minerals or from any mixtures thereof.

20. Nanoparticle according to one or more of items 1 to 19, comprising a diagnostic marker.

21. Nanoparticle according to one or more of items 18 to 20 for use as a medicament or part of a medicament for the oral, pulmonal, nasal, buccal, vaginal or parenteral delivery of a biologically active ingredient or as a diagnostic marker.

22. Pharmaceutical dosage form comprising a multitude of nanoparticles according to one or more of items 18 to 20, wherein the dosage form comprises a pellet, a tablet, a capsule, a spray, an aerosol, a powder, a suppository or an injection solution or dispersion.

EXAMPLES

Materials:

TABLE 1

Structures of acylated human lactoferrin peptides
(hLFF amino acid sequence corresponds to SEQ.
ID. No. 1 = KCFQWQRNMRKVRGPPVSCIKR)

| Material | Supplier |
|---|---|
| $C_{16}$-(mono)acyl human lactoferrin derived peptides | EMC, Tübingen |

Formula 1: Structures of acylated and biacylated human lactoferrin peptides

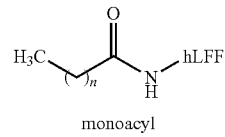

monoacyl

TABLE 2

Chemical compounds used for precipitation test.

| Material | Supplier |
|---|---|
| Hepes | Sigma-Aldrich Chemie GmbH (Taufkirchen, Germany) |

TABLE 3

Chemical compounds used for Fluorescein amine- and Rhodamine-B-PLGA.

| Material | Supplier |
|---|---|
| Rhodamine-B dextran (10000 MW) | LifeTechnologies, Thermo Fisher scientific (Carlsbad, USA) |
| Fluorescein amine isomer I (FA) | Aldrich Chemical Inc. (Milwaukee, Wisconsin; USA) |
| RESORMER ® RG 503 H | Nutrition & Care GmbH (Darmstadt, Germany) |

TABLE 4

Chemical compounds used for preparation of particles.

| Material | Supplier |
|---|---|
| RESOMER ® RG 502 H | Evonik Nutrition & Care GmbH (Darmstadt, Germany) |
| RESOMER ® Select 5050 DLG mPEG 5000 (15%) (RESOMER ® RGP d 50155) | Evonik Nutrition & Care GmbH (Darmstadt, Germany) |
| Mowiol ® 4-88 (poly(vinyl alcohol)/PVA) | Sigma-Aldrich Chemie GmbH (Taufkirchen, Germany) |
| Acetylated bovine serum albumin (BSA) | Thermo Fisher Scientific GmbH (Dreieich, Germany) |
| C2-acetylated human lactoferrin derived peptide (hLFF (C2) or C2-hLFF) = Acetyl-NH-KCFQWQRNMRKVRGPPVSCIKR-CONH2 (amino acid sequence corresponds to SEQ. ID. No. 1) | CS Bio Company (Menlo Park, CA, USA) |
| C16-acetylated human lactoferrin derived peptide (hLFF(C16) or C16-hLFF) = palmitoyl-NH-KCFQWQRNMRKVRGPPVSCIKR-CONH2 (amino acid sequence corresponds to SEQ. ID. No. 1) | EMC (Tübingen, Germany) |
| D-(+)-Trehalose dihydrate, ≥99% | Carl Roth GmbH + Co. KG (Karlsruhe, Germany) |
| Ethyl acetate | Avantor Performance Materials Deutschland (Grießheim, Germany) |
| di-Ammonium-hydrogenphosphate | Merck KGaA (Darmstadt, Germany) |
| Calciumnitrat | Merck KGaA (Darmstadt, Germany) |
| RNAse free water | Life Technologies, Thermo Fisher scientific (Carlsbad, USA) |
| Lumogen F305 Red | BASF (Ludwigshafen, Germany) |

TABLE 5

Chemical compounds used for analytical characterization and biological assays.

| Material | Supplier |
|---|---|
| A549 cells (human lung (carcinoma)) | DSMZ-Deutsche Sammlung von Mikroorganismen und Zellkulturen GmbH (Braunschweig, Germany) |
| HeLa cells | DSMZ-Deutsche Sammlung von Mikroorganismen und Zellkulturen GmbH (Braunschweig, Germany) |
| Caco-2 cells | DSMZ-Deutsche Sammlung von Mikroorganismen und Zellkulturen GmbH (Braunschweig, Germany) |
| MEM (minimum essential medium) | Life Technologies, Thermo Fisher scientific (Carlsbad, USA) |
| PBS (phosphate-buffered saline) | Life Technologies, Thermo Fisher scientific (Carlsbad, USA) |
| RNAse free tubes | various |
| Trypsin | Life Technologies, Thermo Fisher scientific (Carlsbad, USA) |
| Penicillin/Streptomycin | Life Technologies, Thermo Fisher scientific (Carlsbad, USA) |
| Trypan Blue | Life Technologies, Thermo Fisher scientific (Carlsbad, USA) |
| Lipofectamine RNAiMax | Life Technologies, Thermo Fisher scientific (Carlsbad, USA) |

TABLE 6

Devices used for preparation of particles.

| Device | Supplier |
|---|---|
| T 25 digital ULTRA-TURRAX ® with S25N - 10 G and 18 G dispersing element | IKA ®-Werke GmbH & Co. KG (Staufen, Germany) |
| Centrifuge 5415R | Eppendorf AG (Hamburg, Germany) |
| Analytical balance Sartorius ME215S-OCE | Sartorius AG (Göttingen, Germany) |
| Rotary evaporator Heidolph Laborota 4011 digital | Heidolph Instruments GmbH & Co. KG (Schwabach, Germany) |
| Heating thermo shaker HTMR 133 | DITABIS Digital Biomedical Imaging Systems AG (Pforzheim, Germany) |
| Safety cabinet HERA Safe 2020 | Thermo Fisher Scientific GmbH (Dreieich, Germany) |
| Mixer Vortex Genie 2 | Scientific Industries, Inc. (New York, USA) |
| Freeze dryer EPSILON 2-6D AC | Martin Christ Gefriertrocknungsanlagen GmbH (Osterode am Harz, Germany) |

TABLE 6-continued

Devices used for preparation of particles.

| Device | Supplier |
| --- | --- |
| Kendro - Heraeus Herasafe HSP-16 | Thermo Fisher Scientific GmbH (Dreieich, Germany) |
| Variomag Poly | IKA ®-Werke GmbH & Co. KG (Staufen, Germany) |
| Systec-DB-23 | Systec GmbH (Linden, Germany) |

TABLE 7

Devices used for analytical characterization and biological assays.

| Device | Supplier |
| --- | --- |
| Zetasizer Nano ZS | Malvern Instruments GmbH (Herrenberg, Germany) |
| Axio Observer, fluorescence microscope | Carl Zeiss Microscopy GmbH (Jena, Germany) |
| Multiplate-reader TECAN Infinite 200 Pro | Tecan Group Ltd. (Männedorf, Switzerland) |
| Safety cabinet HERA Safe 2020 | Thermo Fisher Scientific GmbH (Dreieich, Germany) |
| HeraCell incubator | Thermo Fisher Scientific GmbH (Dreieich, Germany) |
| Attune Nxt, flow cytometer | Thermo Fisher Scientific GmbH (Dreieich, Germany) |

Methods:

Peptides

All peptides were synthesized as C-terminal amides using solid-phase peptide synthesis (EMC microcollections). For efficient disulfide bridge formation, hLFF peptides were dissolved in 50 mM Hepes buffer pH 8 at a concentration of 2 mM and oxidized for 2 h at 37° C. (Wallbrecher et al., Cell Mol Life Sci. 2014 July; 71(14):2717-29).

Example 1: HLFF-Peptide Precipitation Test hLFF-peptides tested for precipitation by one freeze-thawing cycle (freezing at −18° C.) with hLFF peptides dissolved in 50 mM Hepes buffer pH 8 at a concentration of 2 mM.

Preparation of Fluoresceinamine-PLGA Particles and Rhodamine-B-Ethylene diamine-PLGA Particles.

Fluorescein amine isomer I-PLGA (FA-PLGA) were made by coupling PLGA (RESOMER® RG 503 H, Evonik Industries, Darmstadt, Germany) and Fluorescein amine using the method from Horisawa et al. (Pharm Res. 2002 February; 19(2):132-9) and Weiss et al. (J Nanosci Nanotechnol. 2006 September-October; 6(9-10):3048-56).

Fluorescein amine isomer I (FA) was obtained from Aldrich Chemical Inc. (Milwaukee, Wis., USA). PLGA (3.07 g) and FA (0.0583 g) were dissolved completely in 30 mL of acetonitrile with 0.0408 g of 1-ethyl-3-(3-Dimethyl-aminopropyl)-carbodiimide hydrochloride (WSC), and incubated at room temperature for 2 h. The resultant fluorescein amine bound DL-lactide/glycolide copolymer (FA-PLGA; RESOMER® RG 503 H) was washed with distilled water followed by dichloromethane, and then dried using a rotary evaporator (REN-1S, Iwaki, Osaka, Japan).

For particle preparation, 50 mg of FA-PLGA were dissolved in 1.5 mL of Ethyl Acetate. A (primary) w/o emulsion was prepared by sonication at approximately 6 W for one minute. Then, 2.5 mL of a 25 mg/mL PVA (Mowiol 4-88, Kuraray Europe GmbH, Hattersheim am Main, Germany) solution was added to the emulsion. The mixture was again sonicated at approximately 15 W for 60 seconds resulting in a secondary emulsion. The volume of this emulsion was increased to 20 mL by adding milli-Q. Upon volume increase, the ethyl acetate in the emulsion drops exceeded the non-miscibility border of the two partially soluble solvents and FA-PLGA nanoparticles precipitated from the emulsion.

Lissamine Rhodamine-B-ethylene diamine was obtained from Life Technologies (Darmstadt, Germany) and covalently coupled to PLGA (RESOMER® RG 503 H) (Evonik Industries, Darmstadt, Germany) using the method of Weiss et al. for Fluorescein amine and PLGA with minor changes (J Nanosci Nanotechnol. 2006 September-October; 6(9-10): 3048-56).

Particles were prepared by dissolving 50 mg of Rhodamine-B PLGA (RhB-PLGA) in 1.5 mL Ethyl Acetate. Then 2.5 mL of a 25 mg/mL PVA solution was added and the mixture was sonicated at approximately 16 W for one minute. The volume of the resulting emulsion was increased to 20 mL by adding milli-Q.

Preparation of Lumogen F305 Red labeled PLGA and PLGA/PEG-PLGA particles PLGA (RESOMER® RG 502 H, Evonik Nutrition & Care GmbH, Darmstadt, Germany) and a mixture of PLGA and PEG-PLGA (RESOMER® Select 5050 DLG mPEG 5000 (15%), Evonik Nutrition & Care GmbH, Darmstadt, Germany) were used. The ratio of the mixture (PLGA/PEG-PLGA) is 90:10 w/w. In each formulation, 20 mg were used.

The polymer were dissolved in an ethyl acetate solution with Lumogen R305 Red (0.08 mg mL$^{-1}$, 2250 µL), by using the Vortex mixer. The Lumogen F305 Red concentration depends on the polymer amount and is used as 1% lumogen based on polymer amount. This was the organic solution. The aqueous solution 1 was prepared of calcium nitrate (6.25 mM, 55.85 µL) and di-sodium-hydrogenphosphate (3.74 mM, 55.85 µL), added under continuous mixing with the Vortex mixer (1 min., stage 2-3). This aqueous solution 1 and the BSA solution (20 mg mL$^{-1}$, 20 µL) was added to the organic solution.

An Ultra Turrax T25 was then used at 20 000 min$^{-1}$ for 4 min while being cooled to create the first water-in-oil emulsion (W/O).

This W/O-emulsion was then added dropwise to 1% PVA (9 mL) under constant mixing (Vortex mixer). After addition, the emulsion was further emulsified for 4 min at 15 000 min$^{-1}$ with the Ultra Turrax T25 while being cooled in an ice bath.

The solvent of the W/O/W emulsion was then evaporated at 40° C. and 240 mbar, rotating at 130 rpm for 15 min in a rotary evaporator and for further 90 min under the fume hood at room temperature on a magnetic stirrer with 350 rpm. Afterwards the nanoparticle dispersion was washed by centrifugation at 4° C. and 13 000×g for 10 min. The resulting pellet was resuspended in 10 mL of RNase free water.

hLFF Coating of Particles and Freeze Drying $C_2$-hLFF and $C_{16}$-hLFF peptides (20 mg mL$^{-1}$) were added to 1.0 mL of particle suspension under mixing (Vortex mixer, 1 min., stage 1-2) and incubated for 120 min at 25° C. and 300 rpm in the heating thermo shaker HTMR 133. The final coating of $C_2$-hLFF or $C_{16}$-hLFF was 10% or 50% by weight related to the amount of bio-resorbable polyester. In order to remove excessive hLFF the suspension was centrifuged at 4° C. and 13 000×g for 10 min. The supernatant was discarded and the pellet was resuspended in 2.5 mL of RNase free water.

In order to freeze dry the samples 150 μL of a 50% trehalose solution was added to 3 mL particle suspension, mixed quickly and filled into 4 mL glass vials. These were quick-frozen in liquid nitrogen and then lyophilized using a Christ, freeze dryer EPSILON 2-6D AC.

Particle Size Measurements

In order to analyze the particle size, size distribution and zeta potential, the Zetasizer Nano ZS instrument (Malvern, laser: λ=532 nm) was used with the Smoluchowski approximation. The particle size data refer to scattering intensity distribution (z-average).

Particle size and size distribution were analyzed before and after coating with hLFF using the Zetasizer Nano ZS instrument (Malvern, laser: λ=532 nm).

Cell Uptake Assays

HeLa and Caco-2 cells were incubated with peptide-coated Rhodamine-PLGA particles at a concentration of 0.4 mg mL$^{-1}$ (based on polymer content) for 2 h at 37° C. followed by fluorescence microscopy.

A549 cells were incubated with peptide-coated Lumogen-PLGA and PLGA/PEG-PGLA nanoparticles at a concentration of 0.46 mg mL$^{-1}$ (based on polymer content) for 2 h at 37° C. followed by fluorescence microscopy. Therefore, freeze-dried nanoparticles were resuspended in FBS-free MEM without phenol-red and supplemented with pyruvate, NEAA as well as gentamicin. Untreated and therefore unstained cells were used as negative control.

After washing with PBS, microscopy pictures were taken and cells were detached with 1 mL EDTA/PBS for Flow Cytometry analysis (Sample volume 200 mL; flow rate 100 μL min$^{-1}$; max event counts: $5\times10^4$) and collected in 1.5 mL microcentrifuge tubes.

The microscopic pictures showed that Rhodamine-PLGA-nanoparticles comprising a $C_{16}$-hLFF combine high cellular uptake with little aggregation with HeLa and CaCO-2 cells. The results are superior compared to uncoated nanoparticles and $C_2$-hLFF-nanoparticles.

Results:

Peptide Precipitation Test

Solutions of acylated and biacylated human lactoferrin peptides were tested for precipitation in several freeze-thaw cycles. The results display that only solutions of Acetyl- and C16-hLFF do not precipitate in contrast to all other tested peptides.

Example 2

Particle size distribution of coated particles and their change in zeta potential Table 8 A-F:

Tables 8A, 8B, 8C: FA-PLGA particles comprising acylated (C2, C16) human lactoferrin peptides (all measurements in duplicates). Measurements were performed one, four and eight days after the coating.

Tables 8D, 8E, 8F: Rhodamine-PLGA particles comprising acylated (C2, C16) human lactoferrin peptides (all measurements in duplicates). Measurements were performed one, four and eight days after the coating.

Tables 8A, 8D show the particle sizes Z-Ave values in nm;

Tables 8B, 8E show the particle size distribution (polydispersity index PDI) values;

Tables 8C, 8F show the zeta potential (ZP) values.

TABLE 8A

| [Z-Ave nm] | day 1 | | day 4 | | day 8 | |
| --- | --- | --- | --- | --- | --- | --- |
| | 1 | 2 | 1 | 2 | 1 | 2 |
| uncoated | 194 | 187 | 176 | 184 | 195 | 172 |
| Acetyl (C2) | 209 | 202 | 181 | 182 | 178 | 179 |
| C16 | 195 | 196 | 172 | 189 | 182 | 185 |

TABLE 8B

| PDI | day 1 | | day 4 | | day 8 | |
| --- | --- | --- | --- | --- | --- | --- |
| | 1 | 2 | 1 | 2 | 1 | 2 |
| uncoated | 0.112 | 0.07 | 0.067 | 0.12 | 0.115 | 0.06 |
| Acetyl | 0.108 | 0.21 | 0.152 | 0.08 | 0.128 | 0.09 |
| C16 | 0.123 | 0.14 | 0.072 | 0.11 | 0.107 | 0.12 |

TABLE 8C

| ZP [mV] | day 1 | | day 4 | | day 8 | |
| --- | --- | --- | --- | --- | --- | --- |
| | 1 | 2 | 1 | 2 | 1 | 2 |
| uncoated | −14.1 | −19.3 | −19.1 | −22.4 | −22.3 | −21 |
| Acetyl | 7.8 | 16.4 | 4 | 18.1 | −1.3 | 15.4 |
| C16 | 12.4 | 18.7 | 20.7 | 18.4 | 12.2 | 12.9 |

TABLE 8D

| [Z-Ave nm] | day 1 | | day 4 | | day 8 | |
| --- | --- | --- | --- | --- | --- | --- |
| | 1 | 2 | 1 | 2 | 1 | 2 |
| uncoated | 171 | 168 | 167 | 187 | 260 | 212 |
| Acetyl | 198 | 384 | 165 | 177 | 689 | 175 |
| C16 | 198 | 251 | 402 | 245 | 237 | 533 |

TABLE 8E

| PDI | day 1 | | day 4 | | day 8 | |
|---|---|---|---|---|---|---|
| | 1 | 2 | 1 | 2 | 1 | 2 |
| uncoated | 0.146 | 0.16 | 0.118 | 0.15 | 0.221 | 0.2 |
| Acetyl | 0.235 | 0.32 | 0.187 | 0.19 | 0.347 | 0.15 |
| C16 | 0.211 | 0.31 | 0.33 | 0.34 | 0.263 | 0.4 |

TABLE 8F

| ZP [mV] | day 1 | | day 4 | | day 8 | |
|---|---|---|---|---|---|---|
| | 1 | 2 | 1 | 2 | 1 | 2 |
| uncoated | −17.6 | −27.4 | −23.5 | −25.2 | −22.6 | −21.1 |
| Acetyl | −0.4 | 8.2 | −2 | 3.5 | −1.3 | −9.8 |
| C16 | 16.3 | 25.3 | 9.3 | 13.1 | 6.9 | 4.5 |

Results:

The evaluation of a stable size distribution (target<400 nm), a PDI lower than 0.3 and a zeta potential that is in all cases stably shifted to positive values, shows that only the $C_{16}$-hLFF peptide led to suitable results. C16-hLFF coating of PLGA particles yields small particles of uniform size that maintain a positive zeta potential over time.

Additionally C16-hLFF-coated PLGA particles combine high cellular uptake with little aggregation and are superior to standard acetylated hLFF.

Example 3

TABLE 9

Zeta potential in mV of PLGA and PEG-PLGA nanoparticles coated with acetylated hLFF or $C_{16}$-hLFF; nanoparticles were coated for 30 min (A) or 12 hours (B).

| | $C_2$-hLFF | | $C_{16}$-hLFF | |
|---|---|---|---|---|
| | day 1 | day 3 | day 1 | day 3 |
| A (30 min) | | | | |
| PLGA | 3.38 | 5.93 | 16.8 | 21.4 |
| PEG-PLGA | 4.5 | 5.78 | 17.1 | 19.7 |
| B (12 h) | | | | |
| PLGA | 2.8 | 5.73 | 17 | 25.5 |
| PEG-PLGA | 4.36 | 5.59 | 19.3 | 21.1 |

Results

Furthermore, $C_{16}$-hLFF coating was tested on PEG-PLGA particles in comparison to PLGA and $C_2$-hLFF peptide. Surprisingly $C_{16}$-hLFF yields an improved functionalization of PEG-PLGA in comparison to $C_2$-hLFF. Long-term coating provides only a slightly higher zeta potential.

Example 4

TABLE 10

Particle size (Z-Ave), particle size distribution (PDI) and zeta potential (ZP) of Lumogen labelled PLGA and PLGA/PEG-PLGA nanoparticles coated with hLFF or C16-hLFF.

| | | | | | | Average | | |
|---|---|---|---|---|---|---|---|---|
| Sample name | T °C. | Z-Ave d · nm | PDI | T °C. | ZP mV | Z-Ave d · nm | PdI | ZP mV |
| PLGA without hLFF | 25 | 243.9 | 0.1 | 25 | −31.8 | 239.4 | 0.100 | −31 |
| | 25 | 236.5 | 0.101 | 25 | −31.2 | | | |
| | 25 | 237.8 | 0.098 | 24.9 | −30 | | | |
| PLGA 10% hLFF (C2) | 25 | 242.3 | 0.126 | 25 | 6.3 | 238.5 | 0.153 | 6 |
| | 25 | 237.5 | 0.17 | 24.9 | 5.94 | | | |
| | 25 | 235.6 | 0.162 | 25 | 5.5 | | | |
| PLGA 10% hLFF (C16) | 25 | 237.3 | 0.125 | 25 | 22.6 | 232.8 | 0.153 | 23 |
| | 25 | 234.1 | 0.147 | 25.1 | 22.2 | | | |
| | 25 | 227 | 0.186 | 25.1 | 23 | | | |
| PLGA/PEG-PLGA without hLFF | 25 | 255 | 0.11 | 25 | −26 | 251.5 | 0.097 | −29 |
| | 25 | 251.9 | 0.078 | 25 | −29.8 | | | |
| | 25 | 247.5 | 0.102 | 25 | −29.8 | | | |
| PLGA/PEG-PLGA 10% hLFF (C2)) | 25 | 254.2 | 0.198 | 25 | 5.93 | 249.9 | 0.175 | 6 |
| | 25 | 246.6 | 0.163 | 25 | 5.88 | | | |
| | 25 | 248.9 | 0.164 | 24.9 | 5.88 | | | |
| PLGA/PEG-PLGA 10% hLFF(C16) | 25 | 247.1 | 0.145 | 25 | 24.9 | 239.5 | 0.125 | 25 |
| | 25 | 236.2 | 0.115 | 25 | 25.2 | | | |
| | 25 | 235.3 | 0.116 | 24.9 | 25 | | | |

Example 5

Flow Cytometry Results of Nanoparticle Uptake in A549 Cells

Living cell population of the unstained negative control was gated and set as Lumogen F305 Red-negative cells. A histogram was set up for every measured sample with the relative fluorescence on the x-axis and the number of living cells on the y-axis.

The Median of the x-axis represents the fluorescence intensity of the living cell population and therefore the amount of nanoparticle association and uptake.

Due to the difference in cell counts the relative fluorescence was calculated per 100 cells.

$$\frac{\text{Total counts}}{X \text{ Median}} * 100$$

TABLE 11

Results of flow cytometry analysis

| Sample | X Median (Lumogen) | Total Counts [living cells] | Rel. Fluorescence per 100 cells |
|---|---|---|---|
| PLGA without hLFF | 82 | 17549 | 0.467 |
| PLGA 10% hLFF (C2) | 2108 | 21512 | 9.799 |
| PLGA 10% hLFF (C16) | 60581 | 16812 | 360.344 |
| PLGA 50% hLFF (C2) | 6842 | 7383 | 92.672 |
| PLGA 50% hLFF (C16) | 71806 | 6078 | 1181.408 |
| PLGA/PEG-PLGA without hLFF | 1107 | 10417 | 10.627 |
| PLGA/PEG-PLGA 10% hLFF (C2) | 804 | 6352 | 12.657 |
| PLGA/PEG-PLGA 10% hLFF (C16) | 54816 | 15143 | 361.989 |
| PLGA/PEG-PLGA 50% hLFF (C2) | 4142 | 16856 | 24.573 |
| PLGA/PEG-PLGA 50% hLFF (C16) | 69627 | 1864 | 3735.354 |
| Untreated control | 12 | 21766 | 0.055 |

As shown in the table coating with C16-hLFF led to the highest relative fluorescence values and therefore the best uptake of nanoparticles for both, PLGA/PEG-PLGA and PLGA polymer. Furthermore, the uptake was improved by increasing the amount of hLFF or C16-hLFF from 10 to 50%.

The invention claimed is:

1. A nanoparticle, comprising:
   a core, comprising,
      a bio-resorbable polyester, and
      a hydrophilic polymer,
   wherein the hydrophilic polymer is a portion of the bio-resorbable polyester and/or a separate polymer, and
   an acylated human lactoferrin-derived peptide coating the core,
   wherein the acylated human lactoferrin-derived peptide is a peptide with the amino acid sequence SEQ ID NO: 1 or an amino acid sequence, which does not differ by more than 8 amino acid positions from the sequence SEQ ID NO: 1, and
   wherein the N-terminus of the human lactoferrin-derived peptide is acylated with a $C_{16}$-monoacyl group.

2. The nanoparticle according to claim 1, wherein the bio-resorbable polyester and the hydrophilic polymer is
   i) the bio-resorbable polyester without the hydrophilic polymer portion and the hydrophilic polymer, or
   ii) the bio-resorbable polyester with the hydrophilic polymer portion, or
   iii) the bio-resorbable polyester With the hydrophilic polymer portion and the hydrophilic polymer, or

---

SEQUENCE LISTING

<160> NUMBER OF SEQ ID NOS: 1

<210> SEQ ID NO 1
<211> LENGTH: 22
<212> TYPE: PRT
<213> ORGANISM: Homo sapiens
<220> FEATURE:
<221> NAME/KEY: PEPTIDE
<222> LOCATION: (1)..(22)

<400> SEQUENCE: 1

Lys Cys Phe Gln Trp Gln Arg Asn Met Arg Lys Val Arg Gly Pro Pro
1               5                   10                  15

Val Ser Cys Ile Lys Arg
            20 iv) the bio-resorbable polyester without the hydrophilic polymer portion, the hydrophilic polymer and the bio-resorbable polyester with the hydrophilic polymer portion.

3. The nanoparticle according to claim 1, wherein an amount of the acylated human lactoferrin-derived peptide to the bio-resorbable polyester and the hydrophilic polymer is about 1 to 100% by weight or 5 to 75% by weight of the bio-resorbable polyester and the hydrophilic polymer.

4. The nanoparticle according to claim 1, wherein a ratio by weight of the bio-resorbable polyester to the hydrophilic polymer is from 60:40 to 99.9:0.1.

5. The nanoparticle according to claim 1, wherein an average particle size (Z-Ave) is in a range of about 50 to 900.

6. The nanoparticle according to claim 1, wherein a particle size distribution (PDI) is in a range of 0.5 or less.

7. The nanoparticle according to claim 1, wherein zeta potential of the nanoparticle is about 0 to 50 mV.

8. The nanoparticle according to claim 2, wherein the bio-resorbable polyester without the hydrophilic polymer portion, is a polylactic acid, a polyglycolic acid, a polycaprolactone, a lactic acid-glycolic acid copolymer, a lactic acid-glycolic acid-caprolactone terpolymer, a lactic acid-caprolactone copolymer, a poly dioxanone or a lactic acid-trimethylene carbonate copolymer, or any blend thereof.

9. The nanoparticle according to claim 2, wherein the hydrophilic polymer or the hydrophilic polymer portion is a polyethylene glycol.

10. The nanoparticle according to claim 2, wherein the bio-resorbable polyester with the hydrophilic polymer portion, comprises a poly(lactic acid-co-glycolic acid)-polyethylene glycol) block copolymer with the block structure AB, BA, or ABA,
wherein A is poly(lactic acid-co-glycolic acid) and B is polyethylene glycol), and
wherein the poly(ethylene glycol) comprises from about 0.1 to 25% by weight of the poly(lactic acid-co-glycolic acid)-poly(ethylene glycol) block copolymer.

11. The nanoparticle according to claim 1, wherein the bio-resorbable polyester and the hydrophilic polymer are comprised in a mixture of a poly(D,L-lactide-co-glycolide) copolymer with a proportion of D,L-lactide to glycolide from 60:40 to 40:60 parts per mol and a poly(D,L-lactic acid-co-glycolic acid)-poly(ethylene glycol) AB block copolymer with a proportion of D,L-lactide to glycolide from 60:40 to 40:60 parts per mol,
wherein A is poly(D,L-lactic acid-co-glycolic acid) and B is poly(ethylene glycol), and
wherein the poly(ethylene glycol) comprises from about 10 to 20% by weight of the poly(D,L-lactic acid-co-glycolic acid)-poly(ethylene glycol) AB block copolymer.

12. The nanoparticle according to claim 1, further comprising one or more biologically active ingredients.

13. The nanoparticle according to claim 1, further comprising one or more diagnostic markers.

14. A pharmaceutical dosage form, comprising:
a multitude of the nanoparticle according to claim 12,
wherein the pharmaceutical dosage form is selected from the group consisting of a pellet, a tablet, a capsule, a spray, an aerosol, a powder, a sachet, a suppository, an injection solution, and a dispersion.

15. The nanoparticle according to claim 3, wherein the amount of the acylated human lactoferrin-derived peptide to the bio-resorbable polyester and the hydrophilic polymer is about 25 to 75 by weight.

16. The nanoparticle according to claim 4, wherein the ratio by weight of the bio-resorbable polyester to the hydrophilic polymer is from 95:5 to 99.5:0.5.

17. The nanoparticle according to claim 5, wherein the Z-Ave is in a range of about 200 to 300 nm.

18. The nanoparticle according to claim 6, wherein the PDI is in a range of about 0.09 to 0.19.

19. The nanoparticle according to claim 7, wherein the zeta potential of the nanoparticle is about 5 to 30 mV.

20. A method, comprising:
orally, pulmonally, nasally, buccally, vaginally, or parenterally delivering the one or more biologically active ingredients with the nanoparticle according to claim 12 as a medicament or part of a medicament.

* * * * *